(12) United States Patent
Canos et al.

(10) Patent No.: US 6,344,583 B1
(45) Date of Patent: Feb. 5, 2002

(54) OXIDATION OF KETONES TO ESTERS USING A TIN SUBSTITUTED ZEOLITE BETA

(75) Inventors: Avelino Corma Canos, Valencia (ES); Laszlo T. Nemeth, Palatine, IL (US); Michael Renz, Valencia (ES); Jaime G. Moscoso, Mt. Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/557,302

(22) Filed: Apr. 25, 2000

(51) Int. Cl.$^7$ ................................. C07C 69/02
(52) U.S. Cl. ........................ 560/231; 560/102
(58) Field of Search ................. 560/231, 102

(56) References Cited

PUBLICATIONS

G. Strukul, *Angew. Chem. Int. Ed.*, 1998, 37, 1198–1209.
Jacobson, et al., *J. Chem. Soc. Chem. Comm.*, 888, (1978).
Jacobson, et al., Inorganic Chem., 17, 3055 (1978).
W.A. Herrmann, et al., *J. Mol. Catal.*, 94, 213–223 (1994).
A. Bhaumik et al., *Catal. Lett.*, 40, 47 (1996).

*Primary Examiner*—Paul J. Killos
(74) *Attorney, Agent, or Firm*—John G. Tolomei; Frank S. Molinaro

(57) ABSTRACT

Applicants have developed a process for the oxidation of ketones to esters. The process involves contacting the ketone with hydrogen peroxide and a catalyst at oxidation conditions. The catalyst is a molecular sieve represented by the empirical formula:

$$(M_w Sn_x Ti_y Si_{1-x-y-z} Ge_z)O_2$$

where M is a trivalent metal such as aluminum or boron. These molecular sieves have a microporous three dimensional framework structure of at least $SiO_2$ and $SnO_2$ tetrahedral units, a crystallographically regular pore system and the characteristic x-ray diffraction pattern of zeolite beta.

15 Claims, No Drawings

OXIDATION OF KETONES TO ESTERS USING A TIN SUBSTITUTED ZEOLITE BETA

FIELD OF THE INVENTION

This invention relates to a process for the oxidation of ketones to esters. The process involves contacting the ketone with hydrogen peroxide and a catalyst which comprises a tin substituted molecular sieve at oxidation conditions to form the corresponding ester.

BACKGROUND OF THE INVENTION

Esters and lactones (cyclic esters) have various uses in and of themselves and also can be intermediates in the synthesis of antibiotics, steroids, phermones, fragrances and monomers. In 1899 Adolph Baeyer and Victor Villiger first reported the oxidation of menthone and tetrahydrocarvone to the corresponding lactones. The reaction was carried out using monopersulfuric acid, which was the most powerful oxidant known at that time. There has been considerable interest in the Baeyer-Villiger reaction in academia and in industry with numerous papers being published. See, e.g., G. Strukul, *Angew. Chem. Int. Ed.*, 37,11–98 (1998).

The reaction is usually carried out with organic per-acids. When the oxidant is hydrogen peroxide, there are reports of using transition metal catalysts for the Baeyer-Villiger reaction. For example, Jacobson et al., *J.Chem. Soc. Chem. Comun.*, 888, (1978) and in *Inorg. Chem.*, 17, 3055 (1978), have disclosed the use of molybdenum(VI) peroxocomplexes as catalysts in combination with 98% hydrogen peroxide as the oxidant. W. A. Herrmann, et al., in *J. Mol. Catal.*, 94, 213 (1994) have disclosed that the di-peroxo complex of methyl trioxorhenium is also active for the Baeyer-Villiger reaction. In his paper, Strukul also reports on the use of platinum complexes to carry out the oxidation of ketones in conjunction with 35% hydrogen peroxide. Finally, A. Bhaumik et al., in *Catal. Lett.*, 40, 47 (1996) discloses the use of titanium silicalite (TS-1) as a catalyst for the oxidation of ketones in conjunction with hydrogen peroxide. However, the use of TS-1 gave selectivities to the ester of below 50% with hydroxycarboxylic acids being the major by-products.

In contrast to the work disclosed above, applicants have developed a process for converting ketones to esters or lactones, which uses as the catalyst a tin substituted molecular sieve in conjunction with hydrogen peroxide. The catalyst has an empirical formula on an anhydrous basis of:

$$(M_w Sn_x Ti_y Si_{1-x-y-z} Ge_z)O_2$$

where M represents a metal having a +3 valence such as Al or B and "w" is the mole fraction of M and varies from 0 to about 2x. The value of "x" can be from about 0.001 to about 0.1 while "y" and "z" have, respectively, values of 0 to about 0.1 and 0 to about 0.08. The catalysts of this invention have been found to have higher conversions and virtually exclusive selectivity to the lactones.

SUMMARY OF THE INVENTION

An object of the present invention is the conversion of ketones and especially cyclic ketones to esters and especially lactones. Accordingly, one embodiment of the invention is a process for the oxidation of a ketone to an ester comprising contacting a ketone with hydrogen peroxide and a catalyst at oxidation conditions to provide the corresponding ester, the catalyst comprising a molecular sieve having an empirical formula on a calcined and anhydrous basis of:

$$(M_w Sn_x Ti_y Si_{1-x-y-z} Ge_z)O_2$$

where M is a metal having a +3 valence, "w" is the mole fraction of M and varies from 0 to about 2x, "x" is the mole fraction of tin and varies from about 0.001 to about 0.1, "y" is the mole fraction of titanium and varies from zero to about 0.1 and "z" is the mole fraction of germanium and varies from zero to less than about 0.08 and characterized in that the composition has the characteristic x-ray diffraction pattern of zeolite beta, and when "w", "y" and "z" are all zero, then the molecular sieve is amorphous with short range order or has the characteristic x-ray diffraction pattern of zeolite beta.

This and other objects and embodiments of the invention will become more apparent after a detailed description of the invention.

DETAILED DESCRIPTION OF THE INVENTION

As stated, the present application deals with a process (known as the Baeyer-Villiger reaction) in which ketones are converted to esters. It is preferred to convert cyclic ketones to cyclic esters which are generally called lactones. One essential part of this process is a catalyst which comprises a tin containing molecular sieve having the characteristic x-ray diffraction pattern of zeolite beta and an empirical formula on a calcined and anhydrous basis of:

$$(M_w Sn_x Ti_y Si_{1-x-y-z} Ge_z)O_2$$

"x" is the mole fraction of tin and varies from about 0.001 to about 0.1, "y" is the mole fraction of titanium and varies from zero to about 0.1 and "z" is the mole fraction of germanium and varies from zero to less than about 0.08. However, when "w", "y" and "z" are all zero, then the molecular sieve is either amorphous with short range order or has the zeolite beta structure. The M metals which can be used include but are not limited to aluminum, boron, gallium, and iron; and "w"is the mole fraction of M and varies from 0 to about 2x. These molecular sieves have a microporous three dimensional framework structure of at least $SiO_2$ and $SnO_2$ tetrahedral units, and a crystallographically regular pore system.

These molecular sieves are prepared using a hydrothermal crystallization process in which a reaction mixture is prepared by combining reactive sources of tin, silicon, an organic templating agent, optionally germanium, optionally titanium, optionally a M metal, a fluoride or hydroxide source, optionally hydrogen peroxide and water. The sources of silicon include but are not limited to colloidal silica, amorphous silica, fumed silica, silica gel and tetraalkylorthosilicate. Sources of tin include but are not limited to tin halides, tin alkoxides, tin oxide, metallic tin, alkaline and alkaline earth stannates and alkyl tin compounds. A preferred source is tin tetrachloride. Examples of tin alkoxides include tin butoxide, tin ethoxide and tin propoxide. The organic templating agents include, without limitation, tetraalkylammonium ions such as tetraethylammonium ions, aza-polycyclic compounds such as 1,4-diazabicyclo 2,2,2, octane; dialkyldibenzylammonium ions such as dimethyldibenzyl ammonium ion and bis-piperidinium ions such as 4,4' trimethylene bis (N-benzyl N-methyl piperidinium) ion. These ions may be added as the hydroxide or halide compounds. Germanium sources include germanium halides, germanium alkoxides and germanium oxides. Titanium sources include titanium alkoxides and titanium halides. Preferred titanium alkoxides are titanium tetraethoxide, titanium isopropoxide and titanium tetrabutoxide. When M is aluminum, the sources of aluminum include but are not limited to aluminum oxides, such as pesudo-boehmite, aluminum alkoxides such as aluminum isopropoxide, sodium aluminate and aluminum trichloride, with pseudo-boehmite and aluminum alkoxides being preferred. Sources of boron, gallium and iron include oxides, hydroxides, alkoxides, nitrates, sulfates, halides, carboxylates and mixtures thereof. Representative compounds include without limitation boron alkoxides, gallium alkoxides, iron (II) acetate, etc.

The reaction mixture will also contain either a fluoride source such as hydrofluoric acid or ammonium fluoride or a hydroxide source such as sodium hydroxide or potassium hydroxide. The hydroxide source may also be added by using the hydroxide compound of the templating agent. Water is also added to the mixture and optionally hydrogen peroxide.

Generally, the hydrothermal process used to prepare the tin containing molecular sieves involves forming a reaction mixture, using the sources stated above, which is expressed by the formula:

$$SiO_2:kM_2O_3:aR_2O:bSnO_2:cGeO_2:dTiO_2:eF:fH_2O_2:gH_2O$$

where "k" has a value from zero to about 0.1, "a" has a value from about 0.06 to about 0.5, "b" has a value from about 0.001 to about 0.1, "c" has a value from zero to about 0.08, "d" has a value from 0 to about 0.1, "e" has a value from about 0.1 to about 2, "f" has a value from zero to about 0.5 and "g" has a value from about 4 to about 50. The reaction mixture is prepared by mixing the desired sources of tin, silicon, optionally titanium, optionally germanium, optionally a M metal, an organic templating agent, water, optionally hydrogen peroxide and a fluoride or hydroxide source in any order to give the desired mixture. It is also necessary that the pH of the mixture be in the range of about 6 to about 12 and preferably in the range of about 7.5 to about 9.5. If necessary the pH of the mixture can be adjusted by adding HF, $NH_4F$, NaOH, KOH, etc. Hydrogen peroxide may be added in order to form a complex with titanium and maintain it in solution.

Having formed the reaction mixture, it is next reacted at a temperature of about 90° C. to about 200° C. and preferably 120° C. to about 180° C. for a time of about 2 days to about 50 days and preferably from about 10 days to about 25 days in a sealed reaction vessel under autogenous pressure. After the allotted time, the mixture is filtered to isolate the solid product, which is washed with deionized water and dried in air.

In order to promote crystallization of the zeolite beta phase, it is preferred to add zeolite beta crystals as seeds to the reaction mixture. These crystals can be added as a dry solid, a suspension in an appropriate liquid, e.g., water, alcohol or a preorganized gel, i.e., a gel which contains nuclei. A preferred zeolite beta seed is one prepared according to the teachings of Spanish Patent Application No. P9501552.

The isolated molecular sieve is characterized in that it has the x-ray diffraction pattern characteristic of zeolite beta which includes at least the peaks and intensities presented in Table A. The intensity presented in Table A is a relative intensity which is obtained by relating the intensity of each peak (I) to the strongest line ($I_o$). The intensity is given by the equation $100 \times I/I_o$ and are represented by vs, s, m and w, where these are defined as: vs=80–100; s=60–80; m=15–60 and w=0–15.

| 2 Θ | d (Å) | Relative Intensity |
|---|---|---|
| 7.22 | 12.23 | m |
| 7.76 | 11.38 | s |
| 21.54 | 4.12 | m |
| 22.57 | 3.94 | vs |
| 22.96 | 3.87 | w |
| 25.45 | 3.50 | w |
| 27.00 | 3.30 | w |
| 29.00 | 3.08 | w |
| 29.65 | 3.01 | m |
| 30.60 | 2.92 | w |

When the only elements which are present in the framework are Sn and Si, the molecular sieve can either have the zeolite beta structure or be amorphous with short range order. The amorphous composition has the characteristics of the material described in U.S. Pat. No. 3,556,725.

As synthesized, the molecular sieves of this invention will contain some of the organic templating agent and fluoride ions in the pores of the sieve. In order to activate the zeolite, i.e., active for adsorption or catalytic reactions, it is necessary to remove the organic template and fluoride. This is generally accomplished by calcining the molecular sieve at a temperature of about 300° C. to about 1000° C. for a time sufficient to remove substantially all the organic template and fluoride which usually is about 1 to about 10 hrs.

As stated, the molecular sieves described above have very good activity as catalysts for the oxidation of ketones to esters. Examples of ketones which can be used in the instant process include, without limitation, alkyl ketones, cyclic ketones, alkyl substituted cyclic ketones, aryl ketones and alkyl aryl ketones. Specific examples include cyclopentanone, cyclohexanone, methyl cyclopentanone, methyl cyclohexanone, n-pentylcyclopentanone, t-butyl cyclohexanone and adamantanone.

The process involves contacting the ketone with a catalyst (as described above) and hydrogen peroxide at oxidation conditions. Oxidation conditions for the instant process include a temperature of about 20° C. to about 120° C., and preferably about 40° C. to about 90° C., a pressure of about atmospheric to about 400 kPa, and a contact time of about 10 min. to about 24 hours and preferably a time of about 1 hour to about 12 hours. As stated, it is also required to use hydrogen peroxide. Hydrogen peroxide can be obtained as a solution having a concentration of about 3% to about 70% of $H_2O_2$ by weight of the solution. Any of these commercially available solutions can be used in the instant process with a 35% solution being preferred. The ketone may be present neat or it can be mixed with a solvent, with the use of a solvent being preferred. Examples of solvents which can be used include but are not limited to alcohols, ethers, acetals and acetonitrile.

The process can be carried out in either a batch mode or a continuous mode. In a batch mode, the catalyst, ketone and $H_2O_2$ are mixed in a suitable reactor preferably with stirring at the desired temperature for a time of about 10 min. to about 24 hours and preferably a time of about 1 hour to about 12 hours. Whether a batch or continuous mode is used, the molar ratio of $H_2O_2$ to ketone can vary from about 2:1 to about 0.1:1 and preferably from about 1:1 to about 0.3:1. In a continuous mode, the catalyst can be used as a fixed bed, fluidized bed, moving bed, or any other configuration known to one of ordinary skill in the art. When a fixed bed is used, the ketone and hydrogen peroxide can be flowed in either an upflow or downflow direction. The $H_2O_2$ and ketone can be injected separately or can be premixed and then injected into the reactor. Regardless of how the reactants are introduced and the type of bed being used, the reactants are flowed through the reactor at a liquid hourly space velocity (LHSV) of about 0.05 to about 10 hr$^{-1}$ in order to insure adequate contact time between the reactants and the catalyst. Finally, regardless of whether a batch or continuous process is used, the products, reactants, and any formed byproducts are separated by means well known in the art.

In order to more fully illustrate the invention, the following examples are set forth. It is to be understood that the examples are only by way of illustration and are not intended as an undue limitation on the broad scope of the invention as set forth in the appended claims.

EXAMPLE 1

This example illustrates the preparation of zeolite beta seeds according to Spanish patent application no. P9501552.

In a container there were dissolved 1.85 grams of AlCl$_3$.6H$_2$O in 4.33 grams of water. To this solution 45.24 grams of tetraethylammonium hydroxide (TEAOH) (35% by weight aqueous solution) were added. Next, 40 grams of tetraethylorthosilicate (TEOS) were added and the mixture was stirred until the ethanol formed by the hydrolysis of TEOS was evaporated. The final composition of the gel was as follows:

$SiO_2:0.28(TEA)_2O:0.02Al_2O_3:6.5H_2O$

The solution, which was obtained, was transferred to a Teflone®-lined stainless steel autoclave, heated to 140° C., with stirring and reacted for 3 days. The product was recovered by centrifugation, washed with distilled water and dried at 100° C. The product was found to have the structure of zeolite beta with a crystallinity of about 90%.

The zeolite beta sample of the previous paragraph was dealuminated by treating 1 gram of the as-synthesized zeolite with 60 grams of HNO$_3$ (60 wt. %) at 80° C. for 24 hours. The solid was recovered by filtration, washed with distilled water and dried at 100° C. The crystallinity of this product zeolite was found to be 70% and the Si/Al ratio was determined by chemical analysis to be higher than 2,000.

EXAMPLE 2

This example illustrates the synthesis of a stannosilicate with the zeolite beta structure.

In a container, there were added 30 grams of TEOS and 32.85 grams of TEAOH (35 wt. %). After 90 minutes, a solution of 0.21 grams of SnCl$_4$.5H$_2$O (98%) in 2 grams of water was added and the mixture stirred until the ethanol formed by the hydrolysis of TEOS was evaporated. To the clear solution there were added 3.25 grams of HF (48%) and a thick paste was obtained. Finally, a suspension of 0.34 grams of dealuminated zeolite Beta seeds prepared as in Example 1 in 1.85 grams of water was added. The final composition of the gel is described by the following formula:

$SiO_2:0.27 (TEA)_2O:0.004 SnO_2:0.54 HF:7.5 H_2O$

This paste was loaded into a Teflon®-lined stainless steel autoclave and heated to 140° C. and reacted for 10 days with stirring. After this time, the product was recovered by filtration and was shown by x-ray diffraction analysis to have the structure of zeolite beta and to have a crystallinity of about 100%. Chemical analysis further showed that the product contained 0.8 wt. % tin. The product was calcined at 580° C. for 3 hours and maintained its crystallinity. The empirical formula of the product on a calcined and anhydrous basis was determined to be:

$(Si_{0.996}Sn_{0.004})O_2$.

This product was identified as sample A.

EXAMPLE 3

This example illustrates the synthesis of a stannosilicate with the zeolite Beta structure.

In a container, there were added 30 grams of TEOS and 32.99 grams of TEAOH (35 wt. %). After 90 minutes, a solution of 0.43 grams of SnCl$_4$.5H$_2$O (98%) in 2.75 grams of water was added and the mixture stirred until the ethanol formed by the hydrolysis of TEOS was evaporated. To the clear solution there were added 3.2 grams of HF (48%) and a thick paste was obtained. Finally, a suspension of 0.36 grams of dealuminated zeolite Beta seeds prepared as in Example 1 in 1.75 grams of water was added. The final composition of the gel is described by the following formula:

$SiO_2:0.27 (TEA)_2O:0.008 SnO_2:0.54 HF:7.5 H_2O$

This paste was loaded into a Teflon®-lined stainless steel autoclave, heated to 140° C. and reacted for 11 days with stirring. After 11 days, the product was recovered by filtration and was shown by x-ray diffraction analysis to have the structure of zeolite beta and to have a crystallinity of about 95%. Chemical analysis further showed that the product contained 1.6 wt. % tin. The product was calcined at 580° C. for 3 hours and maintained its crystallinity. The empirical formula of the product on a calcined and anhydrous basis was determined to be:

$(Si_{0.992}Sn_{0.008})O_2$.

This product was identified as sample B.

EXAMPLE 4

This example illustrates the synthesis of a stannosilicate with the zeolite Beta structure.

In a container, there were added 30 grams of TEOS and 33.13 grams of TEAOH (35 wt. %). After 90 minutes, a solution of 0.63 grams of SnCl$_4$.5H$_2$O (98%) in 4 grams of water was added and the mixture stirred until the ethanol formed by the hydrolysis of TEOS was evaporated. To the clear solution there were added 3.27 grams of HF (48%) and a thick paste was obtained. Finally, a suspension of 1 gram of dealuminated zeolite Beta seeds prepared as in Example 1 in 4 grams of water was added. The final composition of the gel is described by the following formula:

$SiO_2:0.27 (TEA)_2O:0.012 SnO_2:0.54 HF:5 H_2O$

This paste was loaded into a Teflon®-lined stainless steel autoclave, heated to 175° C. and reacted for 15 days with stirring. After this time, the product was recovered by filtration and was shown by x-ray diffraction analysis to have the structure of zeolite beta and to have a crystallinity of about 95%. Chemical analysis further showed that the product contained 2.3 wt. % tin. The product was calcined at 580° C. for 3 hours and maintained its crystallinity. The empirical formula of the product on a calcined and anhydrous basis was determined to be:

$(Si_{0.988}Sn_{0.012})O_2$.

This product was identified as sample C

EXAMPLE 5

This example illustrates the synthesis of a titanosilicate with the zeolite Beta structure. In a container, 40 grams of TEOS and 1.54 grams of titaniumtetraethoxide were added and to this solution there were added 45.38 grams of TEAOH (35%) and 6.40 grams of hydrogen peroxide (35%). The mixture was stirred until the ethanol formed from the hydrolysis of TEOS was evaporated. To this solution there were added 4.50 grams of HF (48%) and a thick paste was obtained. Finally, a suspension of 0.48 grams of dealuminated zeolite Beta seeds (prepared as in example 1) in 2.3 grams of water was added. The final composition of the gel is described by the following formula:

$SiO_2:0.28\ TEA_2O:0.035\ TiO_2:0.56\ HF:0.34\ H_2O_2:7.5\ H_2O$

This paste was loaded into a Teflon®-lined stainless steel autoclave and heated to 140° C. for 7 days with stirring. After this time, the product was recovered by filtration to give a product which contained silicon and titanium in the framework and had the x-ray diffraction pattern of zeolite beta. The crystallinity of the product as measured from its x-ray diffraction pattern was about 100%. A portion of this sample was analyzed and showed that it contained 1.2 wt. % titanium. After calcination at 580° C. the titanosilicate molecular sieve maintained its crystallinity. The empirical formula of the product on a calcined and anhydrous basis was determined to be:

$(Si_{0.985}Ti_{0.015})O_2$.

This product was identified as sample D.

EXAMPLE 6

This example illustrates the synthesis of an aluminosilicate with the zeolite Beta structure. In a container, 40 grams of TEOS and 30.24 grams of TEAOH (35%) were added. After 90 minutes, a solution of 0.41 grams of metallic aluminum in 16.788 grams of TEAOH was added and the mixture was stirred until the ethanol formed from hydrolysis of TEOS was evaporated. To this solution there were added 4.96 grams of HF (48%) and a thick paste was obtained. Finally, a suspension of 0.34 grams of zeolite Beta seeds (non-dealuminated, Si/Al=25, prepared as in example 1) in 1.3 grams of water was added. The final composition of the gel is described by the following formula:

$SiO_2:0.28\ TEA_2O:0.01\ Al_2O_3:0.56\ HF:7.5\ H_2O$

This paste was loaded into a Teflon®-lined stainless steel autoclave and heated to 140° C. for 1 day with stirring. After this time, the product was recovered by filtration to give product with the x-ray diffraction pattern of zeolite beta and a crystallinity of about 100%. Chemical analysis of the material showed a Si/Al ratio of 50. The product was calcined at 580° C. for 3 hours and its crystallinity was about 95%.

This product was identified as sample E.

EXAMPLE 7

This example illustrates the synthesis of a Sn-silica material.

In a container, 0.95 grams of $SnCl_4.5H_2O$ were added to a solution containing 20 grams of an aqueous solution of cetyltrimethylammonium hydroxide (CTAOH, 0.53M), 6.3 grams of tetramethylammonium hydroxide (TMAOH, 25 wt. %) and 7.6 grams of water. This mixture was stirred at room temperature for 10 minutes and to the resultant solution there were added 4 grams of silica (Aerosil $_{200}$™, Degussa). The reaction mixture was stirred for one hour. The final composition of the gel is described by the following formula:

$SiO_2:0.16\ CTAOH:0.26\ TMAOH:0.04\ SnO_2:24\ H_2O$

The gel was loaded into a Teflon®-lined stainless steel autoclave and heated to 135° C. for 24 hours. After this time, the product was recovered by filtration to give a product which contained silicon and tin.

The occluded organic material was removed by heating the sample under nitrogen flow in a tubular reactor at 540° C. for 1 hour and then in air at 540° C. for 6 hours. A portion of this sample was analyzed and showed that it contained 7.1 wt. % tin.

This product was identified as sample F.

EXAMPLE 8

This example illustrates the synthesis of a Sn-silica material.

In a container, 0.47 grams of $SnCl_4.5H_2O$ were added to a solution containing 10 grams of an aqueous solution of cetyltrimethylammonium hydroxide (CTAOH, 0.53M), 1.94 grams of cetyltrimethylammonium bromide (CTABr), 6.3 grams of tetramethylammonium hydroxide (TMAOH, 25 wt. %) and 16 grams of water. This mixture was heated at 40° C. under gently stirring. When a clear solution was obtained, it was cooled down to room temperature and then there were added 4 grams of silica (Aerosil 200™, Degussa). The reaction mixture was stirred for one hour. The final composition of the gel is described by the following formula:

$SiO_2:0.08\ CTAOH:0.08\ CTABr:0.26\ TMAOH:0.02\ SnO_2:24\ H_2O$

The gel was loaded into a Teflone®-lined stainless steel autoclave and heated to 135° C. for 24 hours. After this time, the product was recovered by filtration to give a product which contained silicon and tin.

The occluded organic material was removed by heating the sample under nitrogen flow in a tubular reactor at 540° C. for 1 hour and then in air at 540° C. for 6 hours. A portion of this sample was analyzed and showed that it contained 3.9 wt. % tin.

This product was identified as sample G.

EXAMPLE 9

This example illustrates the synthesis of a Sn-silica material.

In a container, 0.19 grams of $SnCl_4.5H_2O$ were added to a solution containing 4 grams of an aqueous solution of cetyltrimethylammonium hydroxide (CTAOH, 0.53M), 3.1 grams of cetyltrimethylammonium bromide (CTABr), 6.3 grams of tetramethylammonium hydroxide (TMAOH, 25 wt. %) and 21 grams of water. This mixture was heated at 40° C. under gently stirring. When a clear solution was obtained, it was cooled down to room temperature and then there were added 4 grams of silica (Aerosil $_{200}$™, Degussa). The reaction mixture was stirred for one hour. The final composition of the gel is described by the following formula:

$SiO_2:0.03\ CTAOH:0.13\ CTABr:0.26\ TMAOH:0.008\ SnO_2:24\ H_2O$

The gel was loaded into a Teflon®-lined stainless steel autoclave and heated to 135° C. for 24 hours. After this time, the product was recovered by filtration to give a product which contained silicon and tin.

The occluded organic material was removed by heating the sample under nitrogen flow in a tubular reactor at 540° C. for 1 hour and then in air at 540° C. for 6 hours. A portion of this sample was analyzed and showed that it contained 1.6 wt. % tin.

This product was identified as sample H.

EXAMPLE 10

Samples A to H were tested for the selective oxidation of cyclohexanone to its corresponding lactone as follows. In a round bottomed flask, there were added 3 g of methyl t-butyl ether as a solvent along with one mmol of ketone and a slight molecular excess of hydrogen peroxide (about 1.5 to 2.0 equivalents). Finally, 50 mg of the catalyst to be tested was added and the flask was heated to 56° C. Samples were removed at 1 hour, 3.5 hours, and 6 hours to determine the conversion and selectivity to the corresponding lactone. The activity and selectivity of various catalysts for the conversion of cyclohexanone are presented in Table 1.

EXAMPLE 11

Sample B was tested using the process of Example 10 with various cyclic ketones. These results are presented in Table 2.

TABLE 1

Oxidation of Cyclohexanone by Various Catalysts

| Catalyst I.D. | $H_2O_2$/Cyclo-hexanone (mol/mol) | Conversion (%) | | | Selectivity to Lactone* |
|---|---|---|---|---|---|
| | | 1 hr | 3.5 hr | 6 hr. | |
| A (Sn-β) 0.8% Sn | 2.1 | 9 | 19 | 26 | 100 |
| B (Sn-β) 1.6% Sn | 1.4 | 16 | 23 | 42 | 100 |
| C (Sn-β) 2.3% Sn | 1.5 | 16 | 23 | 25 | 100 |
| D (Ti-β) 1.2% Ti | 1.94 | 2 | 4 | 4 | 100 |
| E (Al-β) Si/Al = 50 | 1.7 | 19 | 19 | 19 | 100 |
| F (Sn-$SiO_2$) 7.1% Sn | 1.6 | 19 | 33 | 33 | 97 |
| G (Sn-$SiO_2$) 3.9% Sn | 1.6 | 4 | 18 | 21 | 88 |
| H (Sn-$SiO_2$) 1.6% Sn | 1.5 | 7 | 16 | 22 | 89 |

*Selectivity at 6 hours

TABLE 2

Oxidation of Various Cyclic Ketones Using a Sn-Beta Catalyst

| Ketone | $H_2O_2$/Ketone (mol/mol) | Conversion (%) | | | Selectivity to Lactone |
|---|---|---|---|---|---|
| | | 1 hr | 3.5 hr | 6 hr. | |
| Cyclopentanone | 1.1 | n.d.* | 19 | 21 | 100 |
| Methyl-cyclopentanone | 1.3 | 15 | 22 | 24 | 100 |
| Cyclohexanone | 1.3 | 14 | 33 | 38 | 100 |
| Methyl-cyclohexanone | 1.4 | 26 | 39 | 44 | 100 |
| n-Pentylcyclopentanone | 1.7 | 7 | 17 | 21 | 100 |
| t-Butyl-cyclohexanone | 1.6 | 33 | 55 | 58 | 100 |
| Adamantanone | 1.6 | 19 | 71 | 84 | 100 |

*not determined

We claim as our invention:

1. A process for the oxidation of a ketone to an ester comprising contacting a ketone with hydrogen peroxide and a catalyst at oxidation conditions to provide the corresponding ester, the catalyst comprising a molecular sieve having an empirical formula on a calcined and anhydrous basis of:

$$(M_w Sn_x Ti_y Si_{1-x-y-z} Ge_z) O_2$$

where M is a metal having a +3 valence, "w" is the mole fraction of M and varies from 0 to about 2x, "x" is the mole fraction of tin and varies from about 0.001 to about 0.1, "y" is the mole fraction of titanium and varies from zero to about 0.1 and "z" is the mole fraction of germanium and varies from zero to less than about 0.08 and characterized in that the composition has the characteristic x-ray diffraction pattern of zeolite beta and when "w", "y" and "z" are all zero, then the molecular sieve is amorphous with short range order or has the characteristic x-ray diffraction pattern of zeolite beta.

2. The process of claim 1 where M is selected from the group consisting of aluminum, boron, gallium, and iron.

3. The process of claim 2 where M is aluminum.

4. The process of claim 1 where "y" has a value of zero.

5. The process of claim 1 where "z" has a value of zero.

6. The process of claim 1 where both "y" and "z" have a value of zero.

7. The process of claim 1 where "w", "y" and "z" have a value of zero.

8. The process of claim 1 where the ketone is mixed with a solvent selected from the group consisting of alcohols, ethers, acetals and acetontrile.

9. The process of claim 1 where the process is carried out in a batch mode with a contact time of about 10 min. to about 24 hours.

10. The process of claim 1 where the process is carried out in a continuous mode at a liquid hourly space velocity of about 0.05 to about 10 $hr^{-1}$.

11. The process of claim 1 where the oxidation conditions include a temperature of about 20° C. to about 120° C. and a pressure of about atmospheric to about 400 kPa.

12. The process of claim 11 where the temperature varies from about 40° C. to about 90° C.

13. The process of claim 1 where the ratio of $H_2O_2$ to ketone varies from about 2:1 to about 0.1:1.

14. The process of claim 13 where the ratio of $H_2O_2$: ketone varies from about 1:1 to about 0.3:1.

15. The process of claim 1 where the ketone is selected from the group consisting of cyclopentanone, cyclohexanone, methylcyclopentanone, methylcyclohexanone, n-pentylcyclopentanone, t-butylcyclohexanone and adamantanone.

* * * * *